United States Patent
Lai et al.

[11] Patent Number: 5,855,550
[45] Date of Patent: Jan. 5, 1999

[54] METHOD AND SYSTEM FOR REMOTELY MONITORING MULTIPLE MEDICAL PARAMETERS

[76] Inventors: Joseph Lai, 19660 Killarney Way, Brookfield, Wis. 53005; Lawrence A. Buyan, 6225 S. 38th St., Greenfield, Wis. 53221; Renee S. DuBore, 8101 Milwaukee Ave., Wauwatosa, Wis. 53213; Brian Lewis Pate, 2042 Bearss Ave. East, Tampa, Fla. 33613; James L. Reuss, 164 S. Charles St., Waukesha, Wis. 53186

[21] Appl. No.: 747,859

[22] Filed: Nov. 13, 1996

[51] Int. Cl.$^6$ .................................................. A61B 5/02
[52] U.S. Cl. ............................................ 600/300; 128/903
[58] Field of Search .................................. 600/300, 368, 600/371, 324, 450, 451, 481, 485, 508, 509, 544, 545, 529, 531, 533, 903

[56] References Cited

U.S. PATENT DOCUMENTS

| | | |
|---|---|---|
| 3,646,606 | 2/1972 | Buxton et al. . |
| 3,786,190 | 1/1974 | Pori . |
| 4,494,553 | 1/1985 | Sciarra et al. . |
| 4,517,982 | 5/1985 | Shiga et al. . |
| 4,556,063 | 12/1985 | Thompson et al. . |
| 4,883,057 | 11/1989 | Broderick . |
| 4,958,645 | 9/1990 | Cadell et al. . |
| 4,981,141 | 1/1991 | Segalowitz . |
| 5,307,817 | 5/1994 | Guggenbuhl et al. . |
| 5,349,953 | 9/1994 | McCarthy et al. ........................ 600/300 |
| 5,381,798 | 1/1995 | Burrows . |
| 5,410,471 | 4/1995 | Alyfuku et al. ......................... 600/300 |
| 5,415,181 | 5/1995 | Hogrefe et al. . |
| 5,416,695 | 5/1995 | Stutman et al. ......................... 600/300 |
| 5,421,343 | 6/1995 | Feng . |
| 5,458,123 | 10/1995 | Unger . |
| 5,462,051 | 10/1995 | Oka et al. .............................. 600/300 |
| 5,536,084 | 7/1996 | Curtis et al. . |
| 5,553,609 | 9/1996 | Chen et al. ............................. 600/300 |
| 5,576,952 | 11/1996 | Stutman et al. ........................ 600/300 |
| 5,617,871 | 4/1997 | Burrows .................................. 600/300 |
| 5,619,991 | 4/1997 | Sloane .................................... 600/300 |

*Primary Examiner*—Robert L. Nasser
*Attorney, Agent, or Firm*—Reinhart, Boerner, Van Deuren, Norris & Rieselbach, s.c.

[57] ABSTRACT

The invention relates to a medical parameter monitoring device which allows the monitoring of a plurality of medical parameters from a remote location. The invention uses a central monitoring system which transmits and receives data parameters via RF from remote patient monitors. The monitoring system utilizes a digital spread spectrum RF transceiver between the central monitoring system to the remote monitors. Forward error correcting, frequency hopping, and spread spectrum communications are employed to provide accurate transmission of data for a plurality of physiological parameters. Transmitted data can be automatically registered into storage in the central monitoring system.

17 Claims, 5 Drawing Sheets

METHOD AND SYSTEM FOR REMOTELY MONITORING MULTIPLE MEDICAL PARAMETERS

BACKGROUND OF THE INVENTION

This invention relates generally to medical parameter monitoring and more particularly to monitoring multiple medical parameters of one or more subjects from a remote location. One preferred embodiment of the invention comprises a patient monitor and transceiver unit in one or more parts, one unit for each of a plurality of patients; a remote display/control device at a central monitoring system; and a communications system between the patient units and the remote display/control device.

Systems presently available for remote monitoring commonly employ either a hardwired connection between the patient monitor and the remote display/control device, or a unidirectional RF transmission from the monitor to remote display/control device only. Typically, analog signal data is transmitted, although digital data can also be encoded and transmitted. The remote display/control device generally supports a number of patient monitors with transmitters, communicating with receivers at the remote display/control device. The patient monitors themselves usually can only monitor one parameter (e.g., ECG), although some systems permit the combination of multiple monitoring devices, sometimes with multiple transmitters per patient. The use of unidirectional analog RF technology limits the patient sensor monitors to performing pre-programmed tasks, with the only control being manual operation of the patient monitor itself. The analog signal quality received at the remote display/control unit tends to be dependent upon the distance from the transmitter to the antenna(e); objects (building components, movable objects, etc.) in between the transmitter and receiver may compromise performance. Furthermore, transmission technologies such as UHF, which employ a particular base frequency for data transmission, face serious problems due to interference from other transmission sources which happen to be transmitting at or near the same frequency.

It is therefore an object of the invention to provide an improved medical monitoring system including a patient monitor and a central monitoring system using bidirectional data transmission.

It is a further object of the invention to provide a novel medical monitoring system that enables dynamic control of remote monitoring simultaneously with medical parameter and/or waveform data acquisition.

It is yet another object of the invention to provide an improved medical monitoring system which can receive and control a plurality of medical parameters and/or waveforms being monitored at remote locations.

It is a further object of the invention to provide a component which can be used therewith to automatically acquire and store data pertaining to various physiological parameters.

It is yet another object of the invention to provide a telemetry system which enables automatic acceptance of patient data and immediate analysis thereof and/or comparison with previously-acquired data.

It is another object of the present invention to use RF communication and automatic registration of critical data, as well as in combination with forward error correcting, frequency hopping, spread spectrum technology, to provide significantly improved results which are surprising and unexpected in view of the prior art.

Other objects, features and advantages of the present invention will be apparent from the following description of the preferred embodiments, taken in conjunction with the accompanying drawings described below wherein like components have like numerals throughout several views.

SUMMARY OF THE INVENTION

Figure 1:
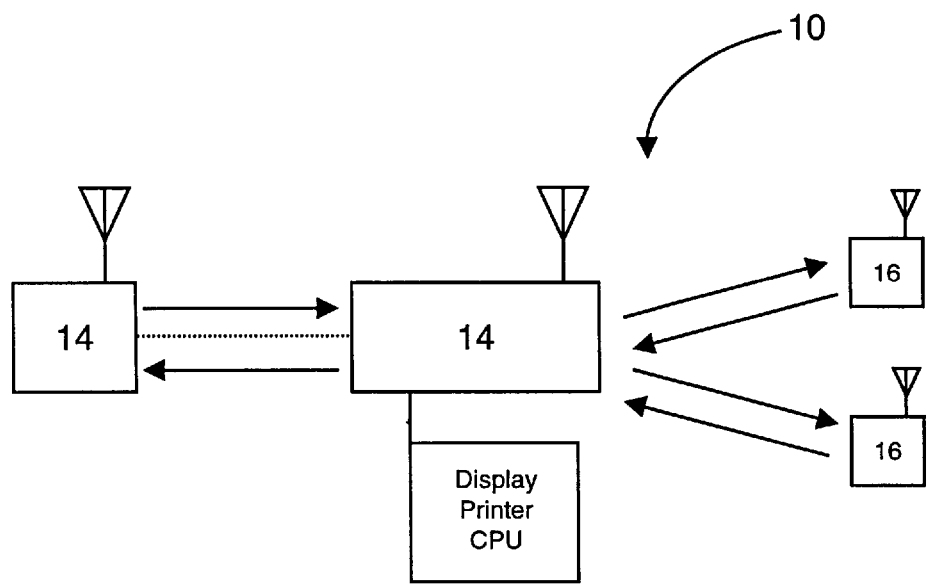
FIG. 1 is a block diagram of a medical monitoring system constructed in accordance with one form of the invention.
Figure 2:
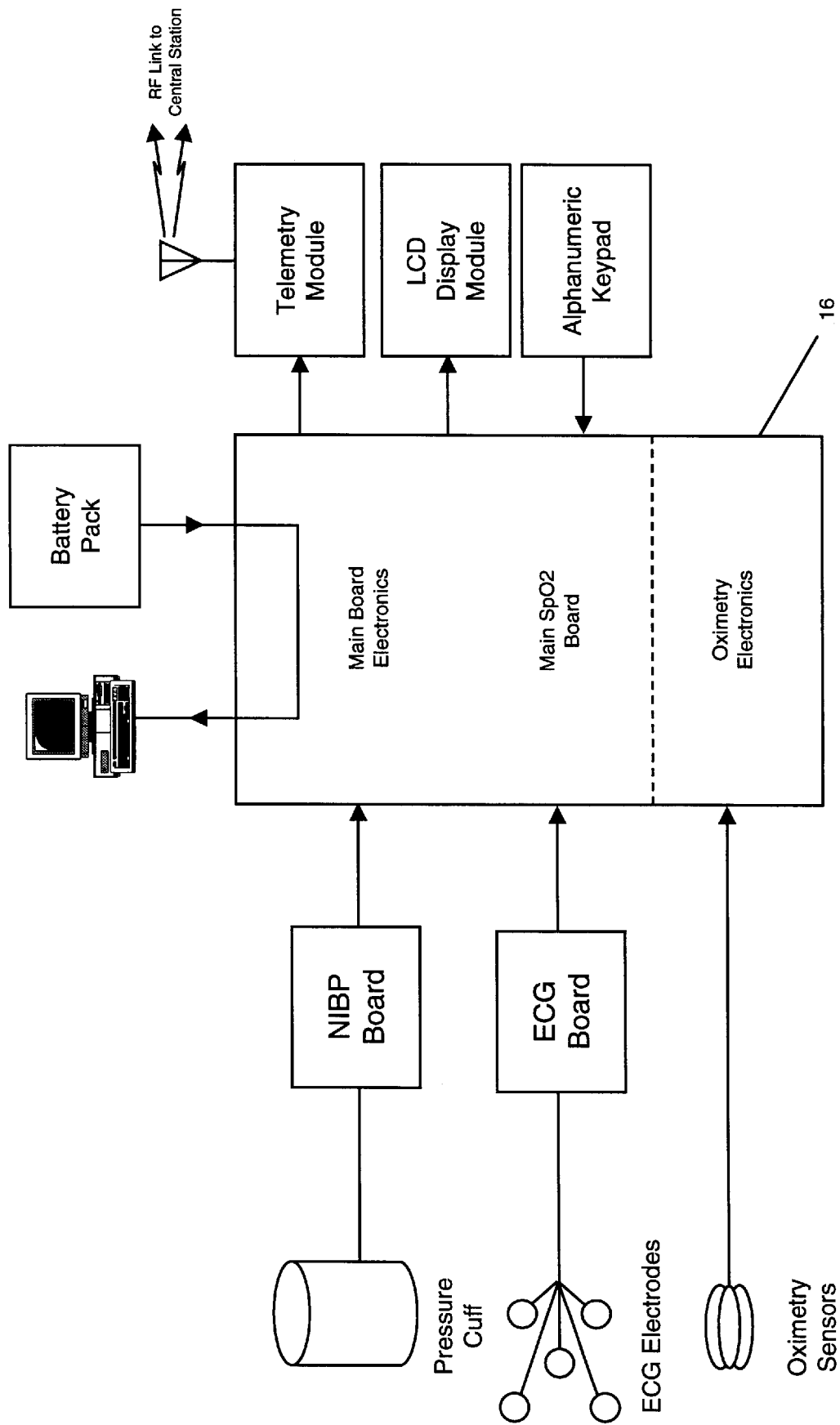
FIG. 2 is a block diagram showing one preferred embodiment of a patient monitor of the present invention.
Figure 3:
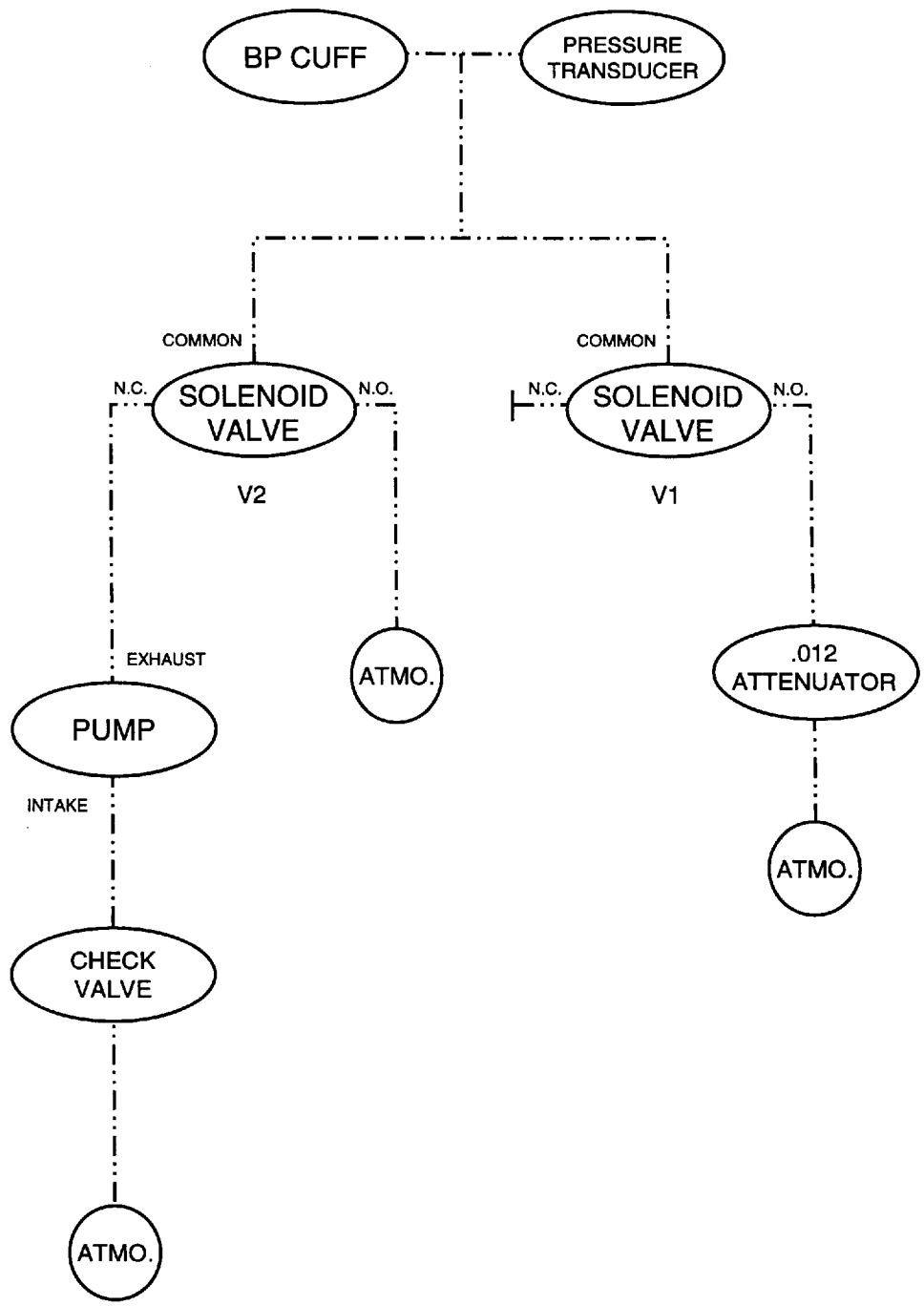
FIG. 3 is a schematic representation of the pneumatic function of a non-invasive blood pressure component of the type which can be used with a preferred embodiment of the invention.
Figure 4:
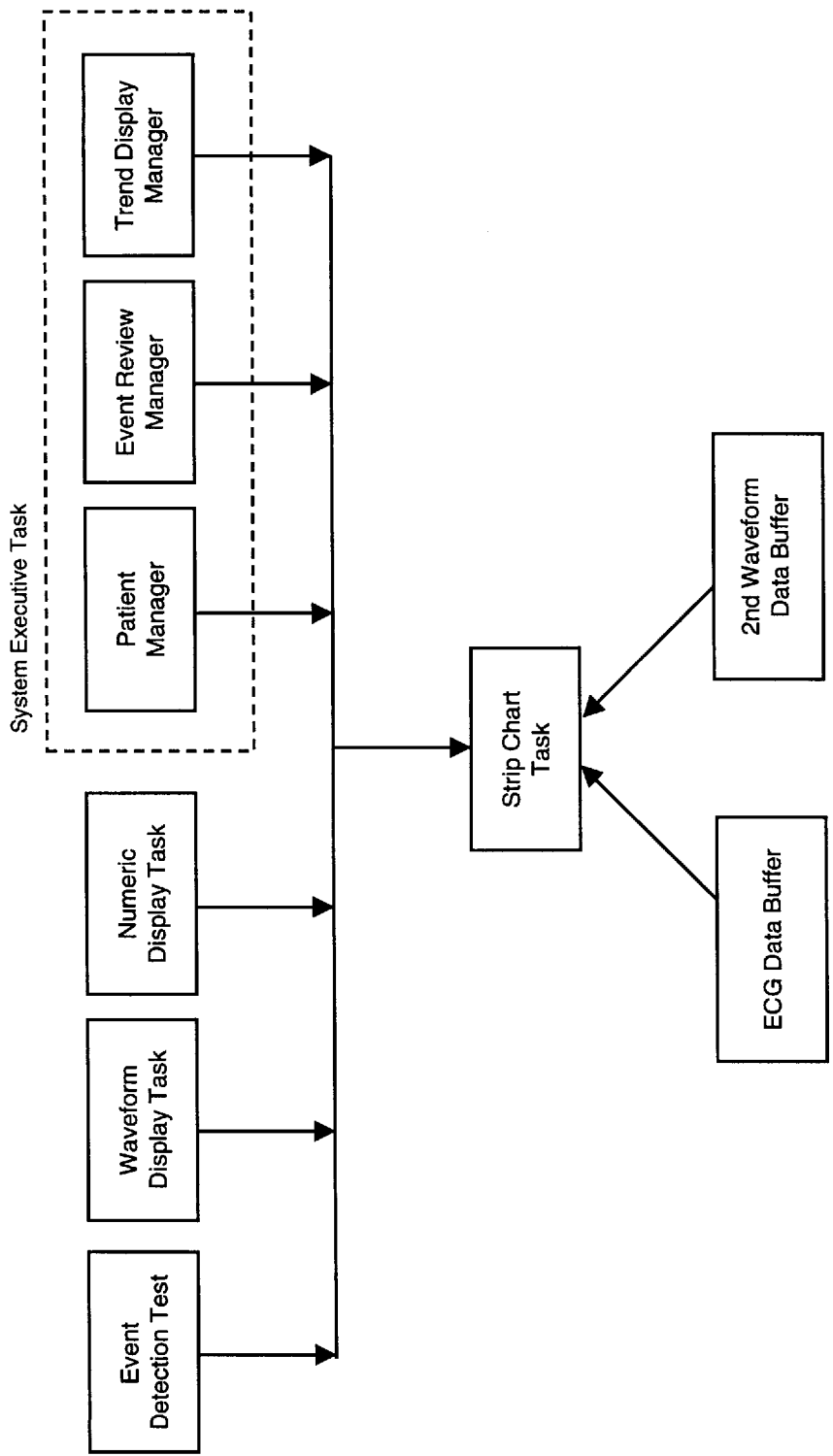
FIGS. 4A, 4B and 4C are block diagrams illustrating software configurations and/or networks of one type which can be used in accordance with the system and/or method of this invention.
Figure 5:
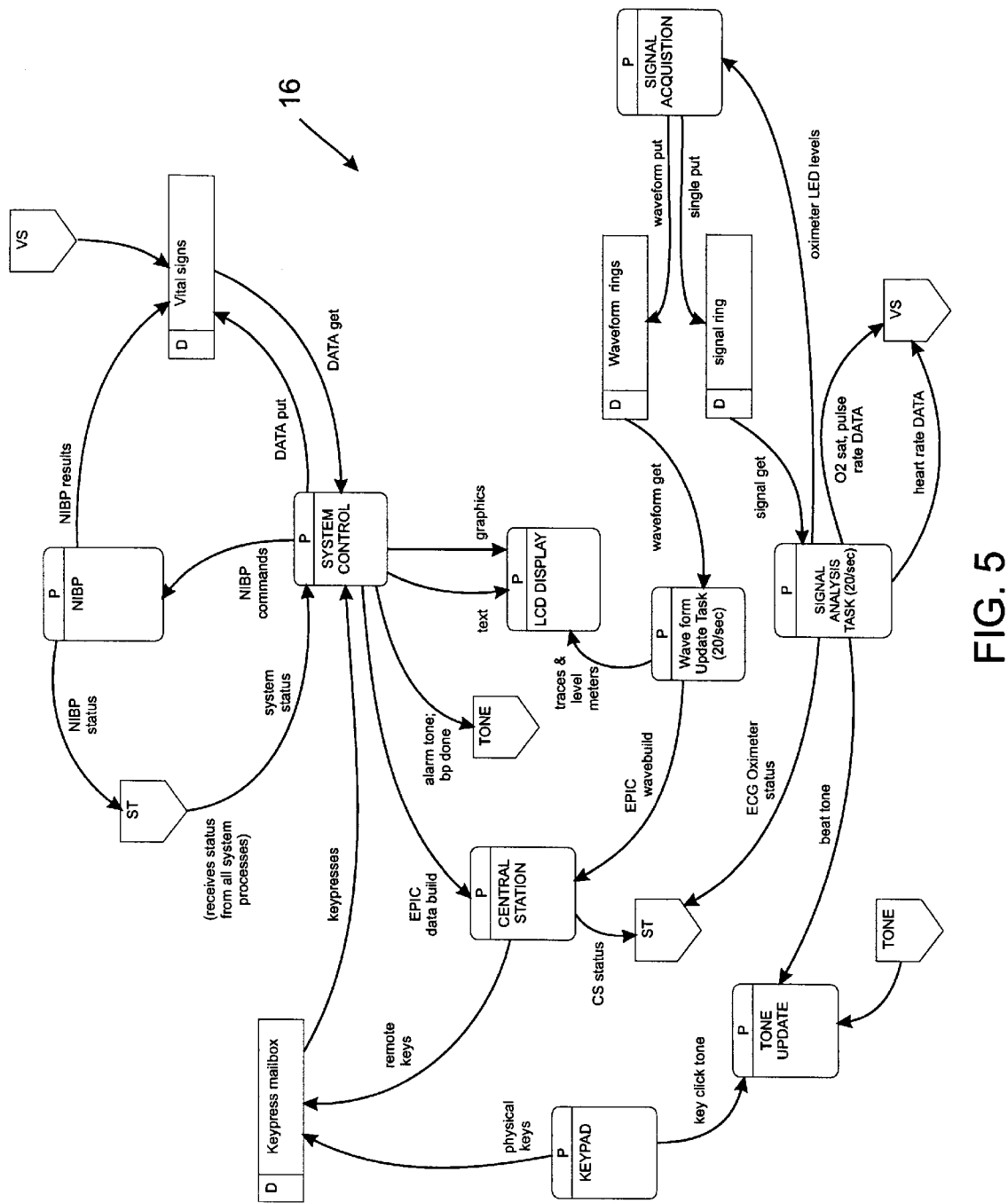
FIG. 5 is a block diagram showing a medical monitoring system constructed in accordance with one form of the invention.

Referring to the figures and more particularly to FIG. 1, a monitoring system constructed in accordance with one form of the invention is shown generally at 10. This preferred embodiment of the invention transmits remotely monitored digital medical data using bidirectional, preferably spread-spectrum RF transmission of digital data which can include forward error correction. Bidirectional transmission permits a remote display/control device 12 of a central monitoring system system 14 to control the monitoring process completely, including selection of medical parameters and/or waveforms to be determined by a patient monitor 16 borne by the patient or located at bedside. This ability to control the patient monitor 16 is important in supporting a broad range of different types of patient monitors 16, from small ambulatory monitoring devices to large bedside monitors with a broad assortment of monitoring capabilities. By permitting dynamic configuration, the mix of patient monitors 16 can change to suit the current patient population. A further feature of this preferred embodiment is the ability to identify the location of a patient being monitored by the system. Additionally, these bidirectional capabilities enable messages to be sent directly from the central monitoring system 14 or devices coupled thereto to the patient monitor 16 or devices coupled thereto. For example, a nurse can respond to a call signal initiated by the patient by sending a message from the central monitoring system 14 to an alphanumeric display at bedside. Methods for direct digital signal formation from input signals produced by a sensor device can be used with preferred embodiments of the invention, and U.S. patent application Ser. No. 08/683,617 is incorporated by reference herein in its entirety for further details regarding such digital signal formation techniques and its incorporation as part of a combination of elements.

The present invention also offers automatic patent physiological registration of the patients through RF communication once the patient monitors 16 are connected to the patient as described below. This facilitates an immediate acquisition of any and all parameters and/or waveforms associated with the central monitoring system which may be applicable to the respective patient. These parameters and/or waveforms can comprise ECG, NIBP, $SpO_2$, respiration, temperature, four invasive lines, alarms, remote recording, and transmitter ID number, as well as other relevant patient information. Further, the bidirectional capabilities of the present invention allow selection of which parameters or waveforms to monitor with patient monitors 16 from the remote, central monitoring system 14. Additionally, the data sampling rates and all other monitoring parameters can be changed remotely using the central monitoring system 14.

As mentioned above and as shown in the figures, the present invention can include an automated data acquisition and/or storage component. Such a component, in its various embodiments, can without limitation be incorporated for use in conjunction with the clinical analysis of transmitted data. This component accommodates automatic patient admission and facilitates the immediate transfer/receipt of data to a central central monitoring system. When a patient is connected to a telemetry transmitter, clinical data is at once available and can be analyzed for various diagnostic purposes. This aspect of the invention can allow for the immediate clinical presentation and analysis of ECG, NIBP, $SO_2$, as well as other pertinent information. This automated component is preferably located in the central monitoring system 14 although it can be located in or coupled to one or more of the patient monitors 16 or other devices.

By way of comparison, the prior art—affording a telemetry interface limited to one or two parameters—is somewhat restrictive in that a central monitoring system must wait for manual acceptance of data transmitted to a central station. For example, an end user of the prior art must manually instruct a central receiving location to learn a transmitted ECG pattern before such data is available for further comparison and analysis. The acceptance delay inherent to the prior art can cause valuable clinical data to be irretrievably lost. In other instances, with manual acquisition and storage of data, substantial delays may occur before the data is available for evaluation. However, with the present invention, once the patient monitor 16 is activated, data can be acquired, stored and evaluated upon transmission/reception. For example, ECG data can be automatically stored and evaluated for comparison to future output ECG data by a central monitoring system 16.

Referring, in part, to the figures, the data acquisition/storage component of this invention can, alternatively, be described in relation to other invention components. Data describing various physiological parameters can be displayed on conventional computer display monitors interfaced with the central monitoring system 14 or other receiving device hardwired or otherwise communicating with the central monitoring system 14. The central monitoring system 14 preferably includes a printer, a computer monitor, a CPU such as a conventional personal computer and a conventional RF transmitter, an RF receiver or an integral RF transceiver. Automatic physiological registration of the patients is afforded through RF communication once the patient monitor 16 is connected to a patient. This facilitates an immediate acquisition of any and all parameters associated with a host monitor and applicable to a respective patient. Such parameters can include, but are not limited to ECG, NIBP, $SpO_2$, respiration and temperature. Comprehensive trending of such parameters over time is available. A 24-hour trending capability is preferred. The trending can involve single or multiple parameters and is especially useful for cardiorespiratory patients, or those with other cardiovascular abnormalities. Invasive lines, alarms, remote recording and transmitter identification can, without limitation, also be incorporated.

While a variety of spectrums and telemetry techniques can be used satisfactorily, preferably a transmitted event signal is digitized inside a host monitor and transmitted via RF communication using ISM band technology in conjunction with forward correcting, frequency hopping, spread spectrum technology, to the central monitoring system 14 or other component. The event can be a 36-second stored event chosen to bracket the time of the event. If so, the central receiving central monitoring system can provide a display six seconds before the event, six seconds during the event, and for 24 seconds following the event. Other display sequences are possible. The station can also, as needed, incorporate disk drive technology, preferably a 1.44 MB floppy disk drive, which enables a clinician to store and/or retrieve patient data. In preferred embodiments of this sort, the central central monitoring system can analyze and store up to 120 events. Such events can be cataloged in an appropriate manner for easy retrieval, such that a running total of events can be reviewed and, as needed, compared to those events not yet reviewed. Events can also be reprinted, stored on a floppy disk or deleted at any time according to standard operating procedure.

As indicated above, the present invention allows transmission of several physiological parameters simultaneously, through hardwire, RF or other communication in contrast to the prior art, where simultaneous transmission is limited. The present invention overcomes such a limitation, without degradation of signal and without a slowdown in system function. Simultaneous transmission, alone or in conjunction with other components of the present invention, permits maintenance monitoring capabilities during the transport of the patient. For instance, a clinician using the present invention is able to transport the patient in such a way as to continuously monitor both invasive and non-invasive physiological parameters. By way of comparison, an end user of the prior art would necessarily disconnect the patient from a host monitor and reconnect that patient to a second monitor, one especially built for transporting the patient. The advance represented by the present invention assists the administration of health care. Continued, uninterrupted monitoring of all parameters and/or waveforms, both invasive and non-invasive, is possible throughout the transport and completion of a subsequent procedure. Furthermore, if hemodynamic monitoring circuits are involved, dispensing with the need to disconnect a patient will decrease the inclement risk of contamination. The patient can be transported immediately and when required, without delay due to changes in monitoring requirements. The continued, uninterrupted monitoring of all parameters and waveforms can be accomplished in several ways.

In accordance with one preferred embodiment of the invention, a plurality of the central monitoring systems 14 are located throughout a facility and can communicate with one another via hardwire, RF or other communication methods. Transfer of a patient from one central monitoring system 14 to another can be accomplished either by manually initiating a transfer function at the initiating central monitoring system 14, or can be accomplished automatically by sensing when a patient enters a zone allocated to another central monitoring system 14. The manual transfer method has the advantage of requiring personnel to consciously execute the command and monitor the results of the transfer. In this way, no patient is inadvertently lost by the system. Appropriate confirmation can be provided to ensure the transfer has been effectively completed. In accordance with the automatic transfer method, the fields of the central monitoring system 14 preferably overlap so that continuous monitoring from a central location can take place.

Alternatively, monitoring can be switched from central monitoring by the central monitoring system 14 to the patient monitors 16 in transit. When a transfer is completed, the patient can be automatically registered into the appropriate central monitoring system 14 to which the patient is being transferred. Communication between the central monitoring system 14 enable historical patient data to be transferred during or subsequent to the transfer procedure.

While a variety of techniques can be used, preferably the ISM frequency band is divided into a number of discrete channels. Each of the central monitoring system 14 can then operate on its own channel.

In accordance with another preferred embodiment of the invention, the central monitoring systems 14 can be accessed from another remote location, such as a lounge and interrogation of certain patient parameters and waveforms can be initiated. In this way, nurses or other personnel can monitor a patient while performing activities in locations other than a central monitoring system.

A preferred embodiment of the present invention is as presented through the multiple parameter telemetry system available under the MPT trademark from Criticare Systems, Inc. of Waukesha, Wis. The non-invasive blood pressure component of this embodiment utilizes oscillometric measurement upon inflation. It can average less than 40 seconds, standard adult cuff. Various automatic measurement cycles are available. Continuous readings are available for up to five minutes. Operative pressures range from 30–300 mm Hg for adults and 20–150 mm Hg for neonates. Such a component typically has an accuracy of ±2% or ±2 mm Hg over the full range of pressures. The pulse oximetry component has a range of 0–99%, with a resolution of 1%. Typically, accuracy is ±2% (70–99%) and ±3% (50–69%). Dual wavelength LED is a preferred method of operation. The ECG component utilizes band widths of 0.05–100 Hz and 0.5–40 Hz. Heart (pulse) rate is measurable over a range of 20–300 beats per minutes, with updates available from beat to beat. Such a component is accurate to ±1 BPM or 1% (the larger)—ECG and/or ±2 BPM or 2% (the larger)—$SpO_2$ and NIBP. Other parameters and waveforms that can be monitored include invasive blood pressure monitors at multiple sites, respiration monitors, body temperature monitors, inspired and expired $CO_2$ levels in inspired and expired air, $O_2$ levels in inspired and expired air, anesthetic levels including nitrous oxide levels in inspired and expired air. It will be apparent to one of ordinary skill in the art that the patient monitors 16 can include any number of conventional monitoring devices for monitoring these parameters and waveforms. With respect to particular RF specifications, the receiver frequency and transmitter frequency can be ISM 902–928 MHz although any legally permissible frequency range can be used. An internal antenna is preferably used with the frequency hopping spectrum spreading techniques which are well known in the art.

In accordance with another preferred embodiment of the invention, an external RF modem can be used with conventional bedside monitors such as those commercially available from the assignee of the present invention. The external RF modem can be used to communicate with the central monitoring system 14 instead of requiring a specially configured patient monitor 16 including RF transceiver technology.

While preferred embodiments of the invention have been shown and described, it will be clear to those skilled in the art that various changes and modifications can be made without departing from the invention in its broader aspects as set forth in the claims provided hereinafter.

What is claimed is:

1. A method for monitoring a plurality of physiological parameters of a patient, comprising the steps of:

providing at least first and second central monitoring systems for monitoring a plurality of physiological parameters, the central monitoring systems each including a first transceiver;

coupling a patient monitor having a second transceiver to said patient to monitor at least one said physiological parameter;

continually transmitting a first data signal corresponding to said physiological parameters from said patient monitor to said first central monitoring system, the first data signal including a patient location signal;

transmitting a second data signal from said first central monitoring system to said patient monitor to remotely select at least one of the plurality of physiological parameters to monitor;

displaying a continuous representation of at least one physiological parameter on a display coupled to the first central monitoring system;

automatically switching control from the first central monitoring system to the second central monitoring system based on the patient location signal; and displaying a continuous representation of at least one physiological parameter on a display coupled to the second central monitoring system.

2. The method as defined in claim 1, further including the step of switching monitoring control from the first central monitoring system to the patient monitor when the patient is in transit, and automatically switching the control to the second central monitoring system when the patient reaches a new stationary location.

3. The method as defined in claim 1, further including the step of automatically recognizing said patient monitor has established bidirectional communications with the central monitoring system and automatically displaying information based upon said monitoring on said display.

4. The method as defined in claim 1, wherein said first data signal and said second data signal are transmitted simultaneously.

5. The method as defined in claim 1, wherein said medical parameters include at least blood pressure, heart rate, $SpO_2$, respiration and ECG.

6. The method as defined in claim 1 further including the step of automatically transferring monitoring of the patient monitor to the second central monitoring system.

7. The method as defined in claim 1 including the step of manually transferring monitoring of the patient monitor to the second central monitoring system.

8. The method as defined in claim 1, including the steps of storing physiological data in a storage unit in at least one of the central monitoring systems, and displaying an event of a predetermined time period.

9. The method as defined in claim 8, including the steps of displaying a second predetermined time period representing a period prior to the event, and a third predetermined time period representing a period after the event.

10. The method as defined in claim 1, wherein spread-spectrum radio-frequency communications are employed to transmit said first and second data signals.

11. The method as defined in claim 1, including the steps of coupling an input device to said patient monitor, coupling a patient monitor display to said patient monitor, selecting monitoring parameters through said input device, and displaying continuous representations of physiological parameters on the patient monitor display.

12. The method as defined in claim 1, further including the step of using the second data signal to select at least one monitoring parameter.

13. The method as defined in claim 1, further including the step of remotely selecting a sampling rate.

14. The method as defined in claim 1, wherein said continuous representation comprises a numerical level of a real-time physiological parameter.

15. The method as defined in claim 1, wherein said continuous representation comprises a waveform of a real-time physiological parameter.

16. The method as defined in claim 1, further including the step of using a storage unit and a processing unit in at least one of the central monitoring systems to provide comprehensive trending of one or more parameters.

17. The method as defined in claim 1, wherein said first data signal further includes a patient location signal.

* * * * *